United States Patent [19]

Fowles et al.

[11] Patent Number: 4,632,267
[45] Date of Patent: Dec. 30, 1986

[54] OVERMOLDED PORT CLOSURE

[75] Inventors: Thomas A. Fowles, McHenry; Brian C. Green, Vernon Hills, both of Ill.

[73] Assignee: Baxter Travenol Laboratories, Inc., Deerfield, Ill.

[21] Appl. No.: 670,501

[22] Filed: Nov. 13, 1984

[51] Int. Cl.$^4$ .................................. B65D 41/32
[52] U.S. Cl. .......................... 215/253; 215/DIG. 3; 220/266; 604/408
[58] Field of Search .............. 215/253, 252, 258, 346, 215/347, 364, DIG. 3; 604/408, 409, 410, 905; 383/59, 63, 65, 66, 904, 906; 220/214, 356, 359, 352, 266; 206/306, 364; 138/96 R, 96 T, 89

[56] References Cited
U.S. PATENT DOCUMENTS

| 3,509,879 | 5/1970 | Bathish et al. | 604/408 |
| 3,805,986 | 4/1974 | Gaudin | 215/DIG. 3 X |
| 3,986,507 | 10/1976 | Watt | 604/408 |
| 3,994,412 | 11/1976 | Difiglio | 220/266 |
| 4,303,067 | 12/1981 | Connolly et al. | 604/408 |
| 4,430,077 | 2/1984 | Mittleman et al. | 215/253 X |

Primary Examiner—Steven M. Pollard
Attorney, Agent, or Firm—John P. Kirby, Jr.; Paul C. Flattery; Robert M. Barrett

[57] ABSTRACT

A improved port and closure assembly is provided. The closure is overmolded to the port. The closure hermetically seals the port and provides a tamper evident closure. The closure cooperates with the port to provide a band that circumscribes the port after the closure is removed.

17 Claims, 3 Drawing Figures

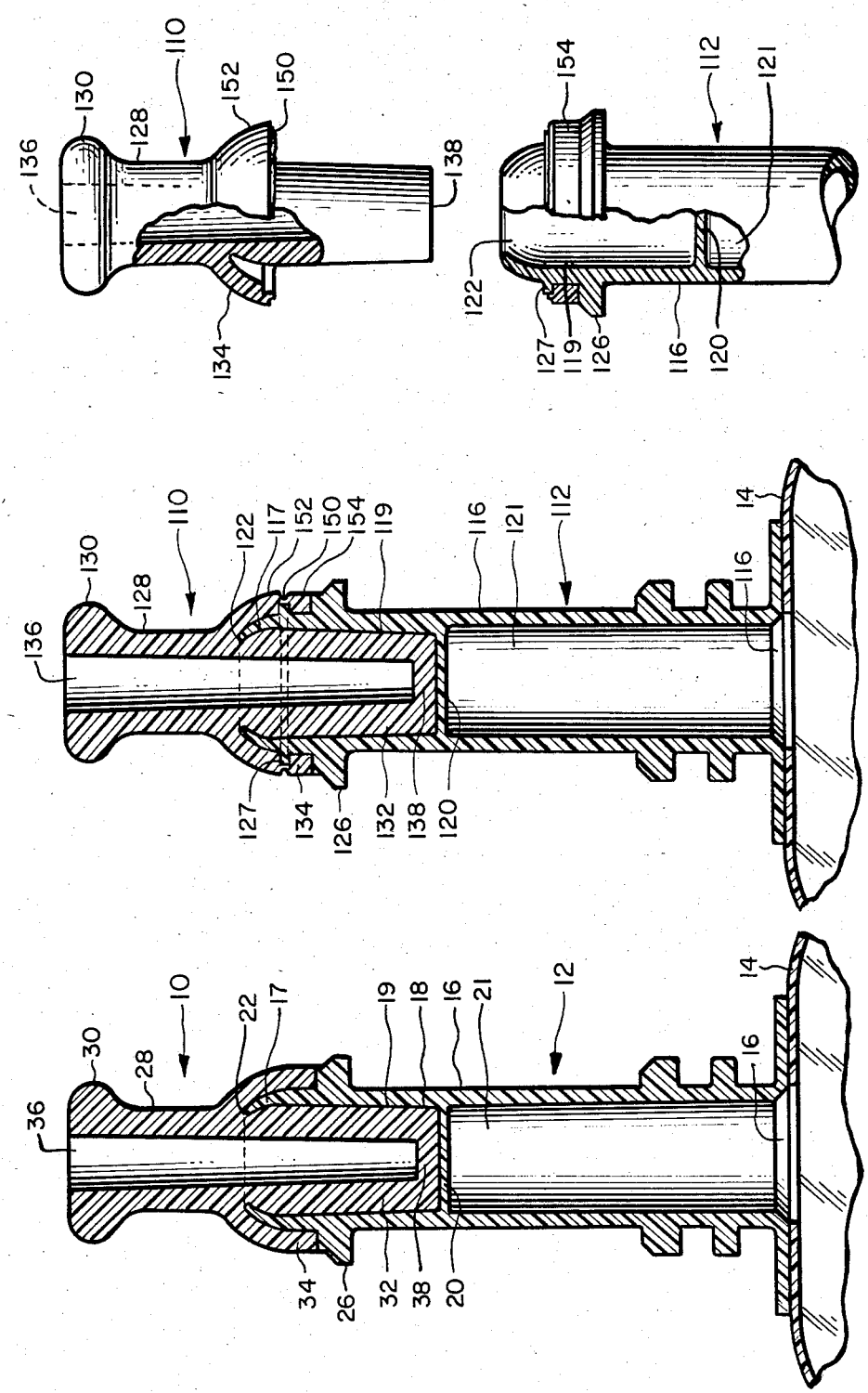

OVERMOLDED PORT CLOSURE

BACKGROUND OF THE INVENTION

This invention relates to a port and closure assembly. In particular, the present invention relates to an integrally molded port closure for sealing a port of a solution container.

Ports are utilized to access material packaged within a container. As used herein, the term ports includes, without limitation, fitments, valves and other means for accessing a container. In the medical industry, parenteral and peritoneal dialysis solutions are packaged in flexible containers that are accessed via a port. An example of such a flexible container is the VIAFLEX ® collapsible plastic container sold by Travenol Laboratories, Inc., of Deerfield, Ill.

In the medical industry particularly, and in other applications, it is essential that the solution in the container is maintained and extracted under sterile conditions. This requires not only that the container and its contents be in a sterile sealed condition at the time of receipt by the user, but also that no contamination of the contents occur when the container is opened by a physician, nurse, or medical technician prior to use. The problem of maintaining sterility is particularly acute at the port of the container.

Typically, the port comprises a tubular structure with an inner bore. Located within the inner bore is a needle pierceable wall that provides a barrier between the fluid contained within the container and the outside environment. Usually, pointed means that pierce the pierceable wall are used to access the fluid and thereby the container. To guard against contamination at the port, closures are utilized for covering the tubular bore of the port.

Some of the problems experienced by the prior art closures are the fact that they do not provide a hermetic seal, are difficult to remove, and do not lend themselves to high speed production. Typically, the process of creating the closure and port assembly includes three steps: molding the port; creating a closure; and fitting the closure on the port. Unless these three steps are performed under aseptic conditions, it is also necessary to sterilize the unit once it is constructed.

Moreover, the closures of the prior art have not provided a satisfactory tamper evident closure. Because it is critical that a sterile environment is maintained, it is advantageous if the closure and port cooperate to provide some means for alerting the user that the closure has been opened and accordingly the aseptic environment violated.

Another problem with prior art closures is the fact that typically they can not be utilized to identify the solution container once the closure is opened. To identify the type of solution contained in the container closures may be color coded. But, once the closure is removed from the port, the container is no longer coded.

Thus, there is a need for a port and closure assembly that overcomes the disadvantages of the prior art.

SUMMARY OF THE INVENTION

The present invention provides an improved port and closure assembly. To this end, the closure is overmolded to the port. This provides a hermetically sealed port. The port and closure may also cooperate to provide a tamper evident closure. To this end, the closure may include a gripping member with a tubular bore, and a stem member with an outer circumference substantially equal to the inner circumference of the port opening.

The closure cooperates with the port to prevent the closure from being easily reinserted into the port after it has been removed. The closure may also be constructed so that it cooperates with the port to provide a band that remains on the port after the closure is removed. This band may function to provide a tamper evident closure, as well as providing a color coded band for identifying the solution in the container.

Accordingly, it is an advantage of the present invention to provide a closure that is overmolded to a port for sealing the port.

Another advantage of the present invention is that it provides a tamper evident closure.

An additional advantage of the present invention is that the closure may not, without great difficulty, be reinserted into the port after it has been removed.

A further advantage of the present invention is that it provides a hermetically sealed closure for a port.

Another advantage of the present invention is that it provides a closure that will leave a color coded band on the port after the closure is removed.

A still further advantage of the present invention is that it provides a more expedient method for creating a port and closure assembly.

A further advantage of the present invention is that it provides a tamper evident closure for a reduced friction port.

Additional features and advantages are described in, and will be apparent from, the Detailed Description of the Presently Preferred Embodiments and from the drawings.

BRIEF DESCRIPTION OF THE DRAWINGS

FIG. 1 illustrates a cross-sectional view of a preferred embodiment of the overmolded port closure of this invention.

FIG. 2 illustrates a cross-sectional view of another preferred embodiment of the overmolded port closure of this invention.

FIG. 3 illustrates a perspective view of the overmolded port closure of FIG. 2 with the closure removed from the port.

DETAILED DESCRIPTION OF THE PRESENTLY PREFERRED EMBODIMENTS

FIG. 1 illustrates the closure 10 of the present invention. The closure 10 is designed to seal a port 12 that provides means for accessing the container 14. The container 14 may be of any type known in the art, and typically is a flexible container made out of plastic or like material. Particularly in medical applications, the container 14 contains a fluid that must be maintained and extracted under sterile conditions. Accordingly, it is critical that sterility be maintained at the port 12.

The port 12 is preferably a reduced friction port as described in U.S. Pat. No. 4,393,909 to Pearson. The port 12 includes an outer wall 16 that defines a tubular bore 18. A partition wall 20 divides the tubular bore 18 into an upper bore 19 and the lower bore 21. The upper bore 19, when the closure 10 does not seal the port 12, is in fluid communication with the outside environment through an opening 22. The opening 22 allows the upper bore 19 to receive a needle or other access means that can pierce the partition wall 20 and thereby access the port 12 and the container 14. The port 12 further includes a rib member 26 that circumscribes the outer wall 16.

To provide a reduced friction port 12 the outer wall 16 includes an inwardly tapered end 17. The inwardly tapered end 17 defines the opening 22.

The closure 10 functions to seal the port 12, and specifically the opening 22. It is especially important in medical applications that this is a hermetic seal so that when the fluid within the container 14 is accessed for intravenous use, the fluid is not contaminated with bacteria or other contaminates. The closure 10 includes an elongated member 28 that is utilized to grip the closure so that it may be removed. In a preferred embodiment illustrated in FIG. 1, the elongated member 28 includes a rib member 30 that circumscribes the top of the elongated member. The closure 10 further includes a stem 32 and a sleeve 34. The stem 32 is designed to be received within the upper bore 19 of the port 12. Preferably, the stem 32 has an outer circumference substantially equal to the inner circumference of the opening 22 of the upper bore 19 so that an intimate friction fit is created. The sleeve member 34 is designed to seal at least a portion of the outer wall 16 of the port 12.

In the preferred embodiment illustrated in FIG. 1, the closure 10 includes a tubular bore 36 extending from the top of the elongated member 28 to the bottom wall 38 of the stem member 32. The tubular bore 36 functions to provide a tamper evident closure 10. To this end, because the stem member 32 has a outer circumference that is substantially equal to the inner circumference of the opening 22 of the upper bore 19, and the fact that the closure 10 includes a tubular bore 36, once the closure 10 is removed from the port 12 it may not be reinserted into the port 12 without great difficulty. This is especially true if the port 12 is of a reduced friction type. Thus, once the closure 10 has been removed from the port 12, one will be readily able to determine that the port has been opened and therefore the sterile environment of the port violated.

Referring now to FIG. 2, another preferred embodiment of the overmolded closure 110 is illustrated. Similarly to the embodiment illustrated in FIG. 1, the closure 110 includes an elongated member 128, a stem 132, and sleeve 134. The port 112 includes an upper bore 119, lower bore 121, outer wall 116, and rib member 126. The closure 110 cooperates with the port 112 to provide a hermetically sealed port.

The sleeve 134 includes a scored line 150 that circumscribes the sleeve. The scored line 150 is designed to circumscribe the sleeve 134 at a position substantially equal to where the rib member 127 underlies the sleeve 134 when the closure 110 seals the port 112. The scored line 150 divides the sleeve 134 into an upper sleeve member 152 and a lower sleeve member 154. The scored line 150 functions to cause the sleeve 134 to separate into an upper section 152 and a lower section 154 as the closure 110 is removed from the port 112.

As illustrated in FIG. 3, when the closure 110 is removed from the port 112 the lower portion of the sleeve 154 remains on the outer wall 116 of the port 112. The lower portion of the sleeve 154 functions as a band that advises the user that the closure 110 has been removed. To this end, the sleeve 134 and specifically the scored line 150 and lower sleeve portion 154 function to provide a tamper evident closure 110.

Moreover, the band 154 may function to identify the solution contained within the container 14. To this end, the closure 110, or just the lower sleeve 154, may be color coded to identify a particular solution. Thus, even though the closure 110 has been removed the port 112 will still be color coded.

The closure 10 and 110 is integrally molded within the port 12 and 112. To this end, in a preferred method of construction, after the port 12 or 112 is injection molded, the closure 10 or 110 is injection molded within the port. The same tool may be utilized for the injection molding of the port 12 and 112 and closure 10 and 110 through the use of a progressive cavity method. A typical progressive cavity method is the typewriter button keys utilizing a multiple head injection molding machine manufactured by Arburg.

The port 12 and 112 and closure 10 and 110 may also be molded through a two shot molding process. Through a two shot molding process the port 12 and 112 is molded and the cavity is then reversed and the closure 10 and 110 is molded on the port 12 and 112.

Through this method of fabricating the port and closure assembly, a ready to use closure assembly will be produced. This eliminates many of the subassembly steps, e.g. quality control of individual parts, inventory of individual parts, and assembly of port and closure. Moreover, because of the injection molding step of the closure 10 or 110 into the port 12 or 112, sterilization of the port may be eliminated. This is due to the fact that the molding temperatures are approximately 350° and will sterilize the upper bore 19 or 119 and outer wall portions 16 and 116 of the port when they are contacted by the closure 10 or 110.

Because the closure 10 and 110 removably seals the port 12 and 112, the closure is constructed from a material that is incompatible with the port. Therefore, when the closure 10 or 110 is integrally molded onto the port 12 or 112 the materials will not cross-link and seal together. Preferably the port 12 or 112 is constructed from polyethylene and the closure is constructed from an ethylene vinyl acetate copolymer. A closure 10 or 110 constructed from a styrene-ethylene-butadiene/styrene radial block copolymer material produced by. Phillips Petroleum Co. and marketed under the trademark SOLPRENE has been found to produce satisfactory results.

By integrally molding the closure 10 or 110 to the port 12 or 112 other advantages are realized. The cost of overmolding the closure 10 or 110 is cheaper and quicker than the prior art methods of constructing the closure and port assembly. Moreover, through overmolding one is assured of a hermetic seal between the closure 10 or 110 and the port 12 or 112.

The closure 10 or 110 produced by the overmolding method lends itself to mechanical assembly in typical production packaging machines. An example of such a machine is the form, fill, and seal packaging machine.

It should be understood that various changes and modifications to the preferred embodiments described herein will be apparent to those skilled in the art. Such changes and modifications can be made without departing from the spirit and scope of the present invention and without diminishing its attendant advantages. It is therefore intended that such changes and modifications be covered by the appended claims.

We claim:

1. A port and closure assembly for a solution container comprising:
    a molded tubular port for providing access to fluid within the solution container, the tubular port including an elongated bore, an outer wall defining the bore, and a rib circumscribing the outer wall;
an overmolded closure for removably sealing the tubular port, including a stem, a sleeve member and a gripping member, the sleeve member extending down the outer wall of the port past the rib, the sleeve being scored along a line circumscribing the sleeve; and
the scored line cooperating with the rib to provide a band that circumscribes a portion of the outer wall of the tubular port after the overmolded closure is removed from the tubular port.

2. The port and closure assembly of claim 1 wherein:
the port is constructed from a polyethylene; and
the closure is constructed from a ethylene vinyl acetate copolymer.

3. The port and closure assembly of claim 1 wherein the sleeve sits on the rib when the closure seals the tubular port.

4. The port and closure assembly of claim 1 wherein the band is color coded.

5. A port and closure assembly for a solution container comprising:
a molded tubular port for accessing fluid within the solution container, the tubular port including an elongated bore, an outer wall defining the bore, and the outer wall including an inwardly tapered end defining an opening and a rib circumscribing the outer wall of the port;
an overmolded closure for removably sealing the tubular port including a stem, a sleeve, and a gripping member having a tubular bore, the sleeve extending down the outer wall of the port past the rib and the sleeve includes a scored line so constructed and arranged that when the closure is removed a portion of the sleeve below the scored line remains on the outer wall of the tubular port; and
the stem being adapted to be received within the opening and the tubular bore and cooperating with the inwardly tapered end of the outer wall of the tubular port to provide a friction fit.

6. The port and closure of claim 5 wherein the overmolded closure and port cooperate to provide a tamper evident closure.

7. The port and closure of claim 5 wherein the closure hermetically seals the port.

8. The port and closure of claim 5 wherein the closure and port are constructed from noncompatible compounds.

9. The port and closure of claim 8 wherein:
the closure is constructed from a ethylene vinyl acetate copolymer; and
the port is constructed from polyethylene.

10. The port and closure of claim 5 wherein the sleeve of the overmolded closure sits on the rib when the closure seals the tubular port.

11. The port and closure of claim 1 wherein the portion of the sleeve below the scored line is color coded.

12. A tamper evident port and closure assembly for a solution container comprising:
a molded tubular port for accessing fluid within the solution container, the tubular port including an elongated bore, an outer wall defining the bore, a rib circumscribing the outer wall of the bore, and the outer wall including an inwardly tapered end defining an opening;
an overmolded closure for removably sealing the tubular port including a stem, a sleeve, and a gripping member having a tubular bore;
the stem being received within the opening and the bore and having an outer circumference substantially equal to the inner circumference of the inwardly tapered end so that a friction fit is created; and
means for producing a band around a portion of the tubular port after the closure is removed.

13. The apparatus of claim 12 wherein the means for producing the band is a scored line circumscribing the sleeve.

14. The apparatus of claim 12 wherein the closure is color coded.

15. The apparatus of claim 12 wherein the band is color coded.

16. The apparatus of claim 12 wherein the port and closure are constructed from incompatible compounds.

17. The apparatus of claim 16 wherein:
the port is constructed from polyethylene; and
the closure is constructed from an ethylene vinyl acetate copolymer.

* * * * *